US012673976B2

(12) United States Patent (10) Patent No.: US 12,673,976 B2

Ma et al. (45) Date of Patent: Jul. 7, 2026

(54) PREPARATION OF CYCLOSPORIN DERIVATIVES

(71) Applicant: Farsight Medical Technology (Shanghai) Co., Ltd., Shanghai (CN)

(72) Inventors: Fashu Ma, Shanghai (CN); Ching-Pong Mak, Shanghai (CN); Daofei Li, Shanghai (CN); Xiao Yu, Shanghai (CN)

(73) Assignee: Farsight Medical Technology (Shanghai) Co., Ltd., Shanghai (CN)

( * ) Notice: Subject to any disclaimer, the term of this patent is extended or adjusted under 35 U.S.C. 154(b) by 785 days.

(21) Appl. No.: 17/906,348

(22) PCT Filed: Mar. 25, 2021

(86) PCT No.: PCT/CN2021/083016
§ 371 (c)(1),
(2) Date: Sep. 15, 2022

(87) PCT Pub. No.: WO2021/190604
PCT Pub. Date: Sep. 30, 2021

(65) Prior Publication Data
US 2023/0174583 A1 Jun. 8, 2023

(30) Foreign Application Priority Data

Mar. 26, 2020 (WO) ................ PCT/CN2020/081295
Mar. 1, 2021 (WO) ................ PCT/CN2021/078391

(51) Int. Cl.
*C07K 7/64* (2006.01)
*A61P 37/00* (2006.01)
(52) U.S. Cl.
CPC ................ *C07K 7/64* (2013.01); *A61P 37/00* (2018.01); *C07K 7/645* (2013.01)
(58) Field of Classification Search
CPC ............ A61P 37/00; C07K 7/645; C07K 7/64
See application file for complete search history.

(56) References Cited

U.S. PATENT DOCUMENTS

| | | | |
|---|---|---|---|
| 6,583,265 B1 | 6/2003 | Ellmerer-Mueller et al. |
| 6,809,077 B2 | 10/2004 | Or et al. |
| 8,481,483 B2 | 7/2013 | Or et al. |
| 12,060,440 B2 | 8/2024 | Mak et al. |
| 2013/0210704 A1 | 8/2013 | Su et al. |
| 2013/0303438 A1 | 11/2013 | Su et al. |
| 2020/0085825 A1 | 3/2020 | Kissel et al. |
| 2023/0173017 A1 | 6/2023 | Peel et al. |
| 2023/0181680 A1 | 6/2023 | Mak et al. |

FOREIGN PATENT DOCUMENTS

| | | |
|---|---|---|
| CN | 101068829 A | 11/2007 |
| CN | 101511357 A | 8/2009 |
| CN | 104768968 A | 7/2015 |
| CN | 104870007 A | 8/2015 |
| CN | 106902346 A | 6/2017 |
| CN | 106902347 A | 6/2017 |
| CN | 109476705 A | 3/2019 |
| CN | 111449050 A | 7/2020 |
| EP | 0194972 A2 | 9/1986 |
| EP | 0484281 A2 | 5/1992 |
| EP | 2751127 B1 | 7/2016 |
| JP | 2001519355 A | 10/2001 |
| JP | 2012516850 A | 7/2012 |
| JP | 2013136597 A | 7/2013 |
| WO | 9918120 A1 | 4/1999 |
| WO | 9965933 A1 | 12/1999 |
| WO | 03033010 A1 | 4/2003 |
| WO | 03033527 A2 | 4/2003 |
| WO | 2004082629 A2 | 9/2004 |
| WO | 2006039668 A2 | 4/2006 |
| WO | 2008143996 A1 | 11/2008 |
| WO | 2010012073 A1 | 2/2010 |
| WO | 2010088573 A1 | 8/2010 |
| WO | 2012079172 A1 | 6/2012 |
| WO | 2016027089 A1 | 2/2016 |
| WO | 2017004304 A1 | 1/2017 |
| WO | 2017200984 A1 | 11/2017 |
| WO | 2019016572 A1 | 1/2019 |
| WO | 2020038426 A1 | 2/2020 |
| WO | 2020147624 A1 | 7/2020 |

OTHER PUBLICATIONS

Written Opinion of International Application No. PCT/CN2021/083016, 6 pages, Apr. 29, 2021.
Written Opinion of the International Application No. PCT/CN2020/081296, 6 pages, Dec. 31, 2020.
Written Opinion of International Application No. PCT/CN2021/083015, 7 pages, Jun. 24, 2021.
Written Opinion of the International Application No. PCT/CN2020/081295, 7 pages, Dec. 31, 2020.
Written Opinion of the International Application No. PCT/CN2021/083013, 8 pages, Jun. 23, 2021.
Devalaraja-Narashimha, Kishor , et al., "Cyclophilin D gene ablation protects mice from ischemic renal injury", Am J Physiol Renal Physiol, vol. 297, Jun. 24, 2009, pp. 749-759.
Klawitter, Jelena , et al., "Cyclophilin D knockout protects the mouse kidney against cyclosporin A-induced oxidative stress", Am J Physiol Renal Physiol; vol. 317, Jun. 12, 2019, pp. 683-694.
Office Action issued in Japan application No. 2022-556478, Apr. 16, 2025, 11 pages.
Office Action issued in Japan application No. 2022-556477, Apr. 16, 2025, 8 pages.
Greene, et al., "Protective Groups in Organic Synthesis", Excerpt from Chapt. 2, Protection for the Hydroxyl Group, Including 1,2- and 1,3-Diols; John Wiley & Sons, Inc., 1999, pp. 208-270.
Hilt, et al., "The Correlation of Lewis Acidities of Silyl Triflates with Reaction Rates of Catalyzed Diels—Alder Reactions", Eur. J. Org. Chem., 2011, pp. 7071-7075.

(Continued)

*Primary Examiner* — Jared Barsky
(74) *Attorney, Agent, or Firm* — Synergy IP Group AG; Lily Ackerman

(57) ABSTRACT

The invention provides a process for the preparation of cyclosporin derivatives.

21 Claims, No Drawings

(56) References Cited

OTHER PUBLICATIONS

Olah, et al., "Improved Preparation of N-Trimethylsilylpyridinium Triflate, N-Triphenylsilylpyridinium Triflate, N-Triisopropylsilylpyridinium Triflate and Their Use in Silylating Alcohols to Silyl Ethers", Synthesis, Issue 7, 1997, pp. 744-746.
Schmaunz, et al., "planpetrer- and Intramolecular [4+2]-Cycloaddition Reactions with 4,4-Disubstituted N-Silyl-1,4-dihydropyridines as Precursors for N-Protonated 2-Azabutadiene Intermediates", Synthesis, vol. 46, 2014, pp. 1630-1638.

PREPARATION OF CYCLOSPORIN DERIVATIVES

CROSS REFERENCE TO RELATED APPLICATIONS

This application is a U.S. National Stage Application filed under 35 U.S.C. § 371 claiming the benefit of International Application No. PCT/CN2021/083016, filed on Mar. 25, 2021, which claims priority to and the benefit of International Application No. PCT/CN2021/078391, filed on Mar. 1, 2021, and International Application No. PCT/CN2020/081295, filed on Mar. 26, 2020, all of which are incorporated herein by reference in their entireties.

BACKGROUND OF THE INVENTION

Cyclosporin A is a compound well known for its immunosuppressive properties. Derivatives of cyclosporin A have also been synthesized and investigated for their biological properties, including derivatives bearing modifications at the sarcosine residue.

For example, U.S. Pat. No. 6,583,265 describes the preparation of cyclosporin compounds with sarcosine substitutions. It is described that cyclosporin compounds substituted with '—O—R3' substituents at the sarcosine position may be prepared by exchanging the sarcosine substituent '—S—R2', with such exchange reaction being effected by metal salts, Lewis acids, or Bronsted acids. With respect to the preparation of the compound [D-Sar-(2-N, N-dimethylaminoethoxy))3]-cyclosporin, it is disclosed that this may be prepared by the reaction of N, N-dimethyl-aminoethanol with 3-(mercaptobenzthiazol-2-ylthio)-cyclosporin in the presence of camphorsulfonic acid. U.S. Pat. No. 6,583,265 does not describe the yield for the preparation of this compound.

WO 2019/016572 A1 also discloses a method for the preparation of this compound, Compound 1:

According to WO 2019/016572, Compound 1 can be obtained by reaction of a thiopyridyl cyclosporin A intermediate with dimethylaminoethanol in the presence of copper triflate and molecular sieves. It is described that this process overcomes the poor reproducibility observed when following the methodology of U.S. Pat. No. 6,583,265. Molecular sieves are used as a drying agent. However, while molecular sieves may be used in the laboratory setting, it is not preferred or practical for production scale processes.

It is thus an object of the present invention to provide an improved and scalable process for the manufacture of Compound 1 and related analogues. Further objects of the invention will be clear on the basis of the following description of the invention, examples, and claims.

SUMMARY OF THE INVENTION

In a first aspect, the invention relates to a process for the preparation of a compound of Formula 1a or a pharmaceutically acceptable salt thereof, Formula 1a wherein the process comprises a step of reacting a compound of Formula 2a Compound 1

Formula 2a

with an amino alcohol in the presence of a copper salt (e.g. copper triflate) and a trialkylsilyl halide.

In a further aspect, the present invention provides for a process for the preparation of Compound 1 or a pharmaceutically acceptable salt thereof:

Compound 1 wherein the process comprises a step of reacting Compound 2

Compound 2

with dimethylaminoethanol, in the presence of a copper salt, such as copper triflate, and a trimethylalkyl halide (e.g. trimethylsilyl chloride).

DETAILED DESCRIPTION OF THE INVENTION

In a first aspect, the disclosure relates to a process for the preparation of a compound of Formula 1a or a pharmaceutically acceptable salt thereof, Formula 1a wherein $R^a$ is ethyl, 1-hydroxyethyl, isopropyl, or n-propyl;

$R^1$ and $R^2$ are independently selected from H, $C_1$ to $C_6$ alkyl, or wherein $R^1$ and $R^2$ are joined together to form a $C_3$ to $C_6$ cycloalkyl or heterocycloalkyl ring;

$R^3$ and $R^4$ are independently selected from H, $C_1$ to $C_6$ alkyl, substituted $C_1$ to $C_6$ alkyl, aryl, substituted aryl, benzyl, carbonyl, carboxyl, sulfonyl; or wherein $R^3$ and $R^4$ are joined together to form a $C_3$ to $C_6$ cycloalkyl or heterocycloalkyl ring;

$R^5$ and $R^6$ are independently selected from H, $C_1$ to $C_6$ alkyl, substituted $C_1$ to $C_6$ alkyl, or wherein $R^5$ and $R^6$ are joined together to form a $C_3$ to $C_6$ cycloalkyl or heterocycloalkyl ring;

wherein the process comprises a step of reacting a compound of Formula 2a with an amino alcohol in the presence of a copper salt and a trialkylsilyl halide;

wherein the compound of Formula 2a is:

Formula 2a wherein $R^a$ is selected from ethyl, 1-hydroxyethyl, isopropyl, and n-propyl; and wherein $R^b$ is aryl, substituted aryl, heteroaryl, or substituted heteroaryl; and wherein the amino alcohol is of Formula 3, Formula 3 wherein $R^1$, $R^2$, $R^3$, $R^4$, $R^5$ and $R^6$ are as defined for Formula 1.

In one embodiment, the cyclosporin compound, intermediate or precursor compound according to the disclosure is a cyclosporin A compound ($R^a$ is ethyl) comprising a substituent at the sarcosine residue at position 3 of the macrocyclic ring such as defined in any one, or combination of the embodiments described herein. In other embodiments, the cyclosporin compound according to the disclosure is a cyclosporin C compound ($R^a$ is 1-hydroxyethyl), a cyclosporin D compound ($R^a$ is isopropyl), or a cyclosporin G compound ($R^a$ is n-propyl), comprising a substituent at position 3, i.e., the sarcosine residue as defined for any one or combination of the embodiments described herein.

The position numbering as used herein refers to commonly used nomenclature and number assignment of the 11 amino acid residues featured in the cyclosporin core. With cyclosporin A as basis, the amino acids residues may be numbered as follows: methyl-butenyl-threonine, which may be abbreviated as MeBmt (1), aminobutyric acid (2)), sarcosine, which may be abbreviated as Sar (3), N-methyl leucine (4), valine (5), N-methyl leucine (6), alanine (7), D-alanine (8), N-methyl leucine (9), N-methyl leucine (10), N-methyl valine (11).

In a further aspect, the disclosure relates to a process for the preparation of a compound of Formula 1b or a pharmaceutically acceptable salt thereof, Formula 1b wherein the process comprises a step of reacting a compound of Formula 2b with an amino alcohol in the presence of a copper salt and a trialkylsilyl halide; wherein the compound of Formula 2b is:

Formula 2b

The term 'H' as used herein refers to hydrogen. The term '$C_1$ to $C_6$ alkyl' as used herein is defined as a saturated or unsaturated alkyl hydrocarbon moiety comprising 1 to 6 carbon atoms in any isomeric configuration. Included are straight-chain, linear alkyl, such as methyl, ethyl, n-propyl, n-butyl, 1-pentyl, n-hexyl. Also included are branched alkyl (i.e. branched $C_3$ to $C_6$ alkyl) such as isopropyl, sec-butyl, isobutyl, tert-butyl, 2-pentyl, 3-pentyl, isopentyl, tert-pentyl, neopentyl, and isomers of hexyl. Further included within the definition of '$C_1$ to $C_6$ alkyl' are cyclic isomers such as cyclopropyl, cyclobutyl, cyclopentyl, and cyclohexyl. Examples of unsaturated $C_1$ to $C_6$ alkyl include but are not limited to vinyl, allyl, butenyl, pentenyl, and hexenyl, and other alkenyl or alkylene moieties, for example comprising one or more double bonds e.g. pentadienyl. The term '$C_3$ to $C_6$' is to be understood analogously but denoting a moiety comprising a range of 3 to 6 carbon atoms.

In one embodiment, $C_1$ to $C_6$ alkyl substituent is an unsubstituted hydrocarbon moiety such as defined above. In an optional embodiment, the $C_1$ to $C_6$ alkyl may be substituted with one or more substituents, whereby one or more hydrogen atoms are replaced with a bond to said substituent or moiety other than hydrogen.

The term 'substituted' such substituted alkyl (e.g. substituted $C_1$ to $C_6$ alkyl for example) may refer to a moiety or radical, wherein one or more hydrogens are replaced, independently, with at least one or more (e.g. two, three, or more) substituents such as halogen, haloalkyl, hydroxyl (—OH), $C_1$ to $C_6$ alkoxyl, amino (—$NH_2$), monoalkylamino, dialkylamino, thioalkyl, nitro, cyano, carbonyl, carboxyl, alkoxycarbonyl, aryl and heteroaryl.

The term 'halogen' is interchangeable with 'halo', or 'halide' and may refer to chloro, bromo, iodo or fluoro atoms. 'Haloalkyl' refers to an alkyl substituent wherein one or more hydrogen atoms are replaced by one or more halogen atoms. An example of haloalkyl is trifluoroalkyl such as trifluoromethyl.

The term 'hydroxyl' refers to a —OH radical. In some embodiments, the hydrogen may be substituted, for example with a hydroxy protecting group within the art. The term 'alkoxyl' or the like means an alkylated hydroxyl substituent, i.e. in which the hydrogen is replaced by an alkyl group. '$C_1$ to $C_6$ alkoxy' refers to the replacement of hydroxy hydrogen with a $C_1$ to $C_6$ alkyl such as defined above. Examples include methoxy, isopropoxy, phenoxy, or t-butoxy.

The term 'amino' may refer to an —$NH_2$ radical. In some embodiments, the hydrogen(s) may be substituted, for example with a protecting group, or one or more further substituent such as alkyl. The term 'monoalkylamino', refers to an amino radical in which one of the hydrogens is replaced with alkyl, e.g. $C_1$ to $C_6$ alkyl such as defined above (i.e. —NHR, wherein R is alkyl). 'Dialkylamino' refers to an amino radical whereby both hydrogens are replaced independently with alkyl (i.e. —NRR', where R and R' are alkyl, which may be the same (e.g. dimethylamino), or different). 'Thioalkyl' may refer to the radical —SR", wherein R" is alkyl, e.g. $C_1$ to $C_6$ alkyl such as defined above. The term 'carbonyl' may refer to the radical —C(O)—$R^c$, wherein $R^c$ may be selected from hydrogen, alkyl, aryl, hetaryl, hydroxy, alkoxy (e.g. —$OCH_3$), amino, alkylamino, dialkyl amino, thioalkyl and the like. The term 'alkoxycarbonyl' or 'carboxyl' may refer to the radical —OC(O)—$R^c$, wherein $R^c$ is selected from alkyl (e.g. $C_1$ to $C_6$ alkyl, e.g. methyl, tert-butyl), aryl, hetaryl, alkoxy, amino, alkylamino, dialkyl amino, thioalkyl, etc.

In some embodiments, two adjacent $R^1$ and $R^2$ substituents (or adjacent $R^5$ or $R^6$ substituents) may be joined together so as to form a ring together, for example a $C_3$ to $C_6$ cycloalkyl ring. "Cycloalkyl" as used herein is a saturated, or unsaturated non-aromatic hydrocarbon ring. Examples of the moieties formed by adjacent $R^1$ and $R^2$ substituents (or adjacent $R^5$ or $R^6$ substituents) joining together to form a ring, for example a cyclopropyl, cyclobutyl, cyclopentyl, and cyclohexyl. In one embodiment, two adjacent $R^1$ and $R^2$ substituents (or adjacent $R^5$ or $R^6$ substituents) are joined to form a cyclopropyl ring.

The term 'hetero' when used to describe a compound or substituent means that one or more carbon atoms are replaced by a oxygen, nitrogen or sulfur atom. In further embodiments of the current disclosure, adjacent substituents such as $R^1$ and $R^2$, or substituents $R^5$ and $R^6$ are joined together to form a heterocycloalkyl ring, for example a $C_3$ to $C_6$ heterocycloalkyl ring. Unless otherwise indicated, 'heterocycloalkyl' refers to a saturated, or unsaturated non-aromatic ring forming at least part of a cyclic structure and where at least one or more carbon atoms are replaced by oxygen, nitrogen or sulfur atom (and in the case of a $C_3$ to $C_6$ heterocycloalkyl comprising between 3 to 6 carbon atoms). For example, the substituents $R^1$ and $R^2$ or substituents $R^5$ and $R^6$ may be joined together to form a may be a 4-, 5- or 6-member saturated, non-aromatic ring comprising at least one heteroatom. The heterocycloalkyl ring may comprise at least one heteroatom selected from O, N, or S.

The substituent $R^a$ of a compound of Formula 1a, 1b, 2a, or 2b may be selected from ethyl, 1-hydroxyethyl, isopropyl, and n-propyl. In one embodiment, $R^a$ is selected from the group consisting of 1-hydroxyethyl, isopropyl, and n-propyl. In another embodiment, $R^a$ is ethyl.

In an embodiment of the disclosed process, $R^1$ and $R^2$ as defined in the Formulas herein are both hydrogen. In another embodiment, at least one of $R^1$ or $R^2$ is $C_1$ to $C_6$ alkyl, e.g. methyl. In a further embodiment, at least one of $R^5$ and $R^6$ of the Formulas as defined herein is hydrogen. Alternatively, $R^5$ and $R^6$ are both hydrogen. In yet another embodiment of a process according to the present disclosure, $R^5$ is $C_1$ to $C_6$ alkyl (e.g. methyl), and $R^6$ is H (hydrogen). In a further embodiment, $R^1$, $R^2$, $R^5$ and $R^6$ are all selected as hydrogen.

In an embodiment according to the present disclosure, $R^3$ and $R^4$ of the Formulas are independently selected from H, $C_1$ to $C_6$ alkyl, substituted $C_1$ to $C_6$ alkyl, aryl, substituted aryl, benzyl, carbonyl, carboxyl, sulfonyl; or wherein $R^3$ and $R^4$ are joined together to form a $C_3$ to $C_6$ cycloalkyl or heterocycloalkyl ring. In a preferred embodiment, IP and $R^4$ are both —$CH_3$ (methyl). In another embodiment of the process, at least one of $R^3$ and $R^4$ as defined in the Formulas herein is methyl. In yet a further embodiment, at least one of $R^3$ and $R^4$ is a carbonyl, or a carboxyl substituent, for example tert-butoxycarbonyl, or similar which may be used to protect the nitrogen group, but which may be later removed for further functionalization of the nitrogen atom.

In another embodiment, $R^3$ and $R^4$ are joined together to form a $C_3$ to $C_6$ cycloalkyl or heterocycloalkyl ring. For example, the substituents $R^3$ and $R^4$ may be joined together to form a 4-, 5- or 6-member saturated, non-aromatic ring. The cycloalkyl ring formed by adjacent $R^3$ and $R^4$ substituents joining together in the context of the compounds of the present Formulas may include, for example azetidine, pyrrolidine, or piperidine. The heterocycloalkyl ring may be a saturated, or unsaturated non-aromatic ring forming at least part of a cyclic structure, where at least one or more carbon atoms are replaced by oxygen, nitrogen, or sulfur atom, in addition to the nitrogen to which $R^3$ and $R^4$ are joined to. The substituents $R^3$ and $R^4$ may be joined together to form a 4-, 5- or 6-member saturated, non-aromatic ring comprising at least one further heteroatom to the nitrogen atom to which they are joined, for example at least one further heteroatom selected from O, N, or S. In one embodiment, $R^3$ and $R^4$ are joined together so as to form a morpholine residue. In an optional embodiment, the cycloalkyl or heterocycloalkyl moiety formed by $R^3$ and $R^4$ may be substituted with one or more substituents such as defined above, where by one or more hydrogen atoms are replaced with a bond to said substituent.

The trialkylsilyl halide as defined in the present invention may be a compound defined by the formula $R^7R^8R^9SiX$, where $R^7$, $R^8$, $R^9$ are independently selected from alkyl substituents (e.g. $C_1$-$C_6$ alkyl) and X is a halide, preferably a chloride. In one embodiment, $R^7$, $R^8$, $R^9$ are the same alkyl substituent. In a preferred embodiment, the trialkylsilyl halide used in the process according to the present disclosure is trimethylsilyl chloride (TMSCl, or (CH₃)SiCl). In one embodiment, a compound of Formula 2a or 2b may be reacted with an amino alcohol of Formula 3 as defined herein in the presence of between 1.0 to 3 equivalents, or between 1.8 to 2.4 equivalents of a trialkylsilyl halide, e.g. trimethylsilyl chloride. In another embodiment, the described reaction processes may be performed in the presence of between 1.8 to 2.4 equivalents of trialkylsilyl halide, e.g. trimethylsilyl chloride.

It has been found that the use of a trialkylsilyl halide such as TMSCl (trimethylsilyl chloride) increases the conversion and yield of the desired reaction product and reduces the loss of starting material (e.g., Compound 2, or compound of Formula 2a or 2b) particularly to the formation of the hydrolysis adduct, e.g. Sar-3-hydroxy cyclosporin. Surprisingly, the reaction may as a consequence be conducted in the absence of molecular sieves (e.g. 3 Å or 4 Å), or a similar type of drying agent.

The compound of Formula 2a or 2b may be reacted with 3 to 5 equivalents of the amino alcohol of Formula 3

Formula 3

$$\underset{R^1 \quad R^2}{\overset{R^5 \quad R^6 \quad R^3}{HO \diagup \diagdown \underset{N}{\diagup} R^4}}$$

wherein R¹, R², R³, R⁴, R⁵ and R⁶ are as defined herein.

In one embodiment, the compound of Formula 2a or 2b is reacted with between 4 to 5 equivalents of the amino alcohol.

In one embodiment, the amino alcohol compound is an amino ethanol compound, wherein R⁵, R⁶, R¹, and R² are selected as hydrogen. In a preferred embodiment, the amino alcohol is dimethylaminoethanol. In other embodiments, at least one of R³ or R⁴ is selected from a C₁-C₆ alkyl, e.g. methyl, ethyl, propyl, isopropyl, n-butyl, sec-butyl, tert-butyl. In other embodiments, at least one of R³ or R⁴ can be selected from more labile substituents, such as carbonyl or carboxyl residue, which can optionally be removed in a downstream process step, for example for further functionalization of the amino substituent.

According to the process as disclosed herein, a compound of Formula 2a or 2b, or Compound 2 is reacted with an amino alcohol compound of Formula 3 in the presence of a copper salt. The copper salt may be a copper (II) salt. In a preferred embodiment, the copper salt is copper triflate. The copper salt, e.g. copper triflate is preferably substantially anhydrous, and may in an embodiment of the process be subjected to pre-processing before use in the reaction to remove any traces of residual water or acid, for example by vacuum drying, optionally under elevated temperatures.

In an embodiment of the process according to the present disclosure, the compound of Formula 2a or 2b is reacted with the amino alcohol in the presence of 3 to 4 equivalents of the copper salt. In a preferred embodiment, the copper salt used in the process according to the present disclosure is copper triflate. In one embodiment, the amount of copper salt (e.g. copper triflate) used in the process is 3.6 equivalents relative to the compound of Formula 2a or 2b.

In one specific embodiment of the process as disclosed herein, a compound of Formula 1a or 1b is prepared by reaction of a compound of Formula 2a or 2b with 3 to 5 equivalents (e.g. 4.2 equivalents) of an amino alcohol of Formula 3 in the presence of 1.8 to 2.4 equivalents (e.g. 2.4 equivalents) of trimethylsilyl chloride and 3 to 4 equivalents (e.g. 3.6 equivalents) of copper triflate.

With respect to the compound of Formula 2a or 2b, the substituent $R^b$ may be aryl, substituted aryl, or heteroaryl or substituted heteroaryl.

The term 'aryl' as used herein refers to carbocyclic ring system having one (monocyclic) or more (e.g. bicyclic) aromatic rings; examples may include, but are not limited to: phenyl, naphthalenyl, anthracenyl, or the like. The aryl ring radical may be joined to the sulfur atom of Formula 2a or 2b at any one its ring atoms. The term 'substituted' aryl refers to an aryl moiety or radical, wherein one or more hydrogen atoms are replaced, independently, with at least one or more (e.g. two, three, or more) substituents including, but not limited to C₁ to C₆ alkyl, halogen, haloalkyl, hydroxyl (—OH), C₁ to C₆ alkoxyl, amino (—NH₂), monoalkylamino, dialkylamino, thioalkyl, nitro, cyano, carboxyl, alkoxycarbonyl, aryl and heteroaryl. The substituent(s) may be featured on any one of the ring atoms of the aryl moiety not joined to the compound.

The term 'heteroaryl' refers to a cyclic aromatic ring system having one or more (e.g. bicyclic, for example) aromatic rings in which one of the ring atoms is replaced by at least one atom selected from S, O and N, with the remaining atoms being carbon. The cyclic aromatic ring system may for example comprise of five to ten ring atoms and may comprise of one, two or more rings. 'Substituted heteroaryl' refers to a heteroaryl moiety wherein one or more hydrogen atoms are replaced, independently, with at least one or more (e.g. two, three, or more) substituents such as defined herein. The heteroaryl radical may be joined to the compound at any of the ring atoms to the compound. Examples of heteroaryl substituents include, but are not limited to pyridine, pyrimidine, pyrazine, thiazole, oxazole, benzothiazole, benzimidazole, furan, quinoline, pyrazole and imidazole, which optionally may also be substituted.

In a further embodiment of the process according to the present invention, the process for the preparation of a compound of Formula 1a, 1b or Compound 1, may comprise a step of reacting a compound of Formula 2a with an amino alcohol in the presence of a copper salt, e.g. copper triflate and a trialkylsilyl halide, wherein the compound is:

wherein $R^a$ is selected from ethyl, 1-hydroxyethyl, iso-
propyl, and n-propyl, and wherein the amino alcohol
compound and trialkylsilyl halide is defined in accor-
dance with any one or combination of embodiments
described herein. Preferably, $R^a$ is ethyl. In a related
embodiment, the copper salt is copper triflate, and the
trialkylsilyl halide is trimethylsilyl chloride.

In yet another embodiment of the process according to the
present invention, the process for the preparation of a
compound of Formula 1a, 1b or Compound 1, may comprise
a step of reacting a compound of Formula 2b with an amino
alcohol in the presence of a copper salt and a trialkylsilyl
halide, wherein the compound is:

wherein $R^a$ is selected from ethyl, 1-hydroxyethyl, iso-
propyl, and n-propyl, and wherein the amino alcohol
compound and trialkylsilyl halide is defined in accor-
dance with any one or combination of embodiments
described herein. Preferably, $R^a$ is ethyl. In a related
embodiment, the copper salt is copper triflate, and the
trialkylsilyl halide is trimethylsilyl chloride.

The present disclosure also further relates to a process for
the preparation of Compound 1 or a pharmaceutically
acceptable salt thereof:

Compound 1 wherein the process comprises a step of reacting Com-
pound 2

Compound 2 with dimethylaminoethanol, in the presence of a copper
salt and a trialkylsilyl halide.

In a preferred embodiment of this process, the copper salt
is a copper (II) salt such as copper triflate, and the trialkyl-
silyl halide is trimethylsilyl chloride.

In another embodiment of this process, between 3 to 5
equivalents of dimethylaminoethanol is reacted with Com-
pound 2. In another embodiment, between 4 to 5 equivalents
of dimethylaminoethanol is used. The amount of copper salt,
e.g. copper triflate used may be between 3 to 4 equivalents.
In a specific embodiment, the amount of copper salt, e.g.
copper triflate used in the reaction process is 3.6 equivalents.
In a further embodiment, Compound 2 is reacted with
dimethylaminoethanol in the presence of 1.8 to 2.4 equiva-
lents of trialkylsilyl halide, e.g. trimethylsilyl chloride.

In a specific embodiment of the process, Compound 2 is
reacted with 4.2 equivalents of the dimethylaminoethanol in
the presence of 2.4 equivalents of trimethylsilyl chloride and
3.6 equivalents of copper triflate.

As used herein, the term 'equivalents' refers to the molar
equivalents relative to Compound 2, or a compound of
Formula 2a or 2b.

The process according to the present invention is, in one
embodiment, performed in anhydrous THF (tetrahydro-
furan) as a reaction solvent or medium. The reaction may be conducted under an inert atmosphere. The reaction may also
be conducted at room temperature conditions (e.g. between 20-25° C.). Preferably, the reaction is performed under substantially anhydrous conditions. Optionally, any one of the reagents, intermediates or starting materials may be dried or processed to remove traces of water before being introduced into the reaction process.

In a further aspect, the disclosure relates to a process for the preparation of a compound of Formula 1a, or Formula 1b, Compound 1 or a salt thereof, wherein the process comprises the steps of:

a) reacting cyclosporin A with a disulfide compound (e.g. pyridyl disulfide), in the presence of a base; and b) reacting a product of step a) with dimethylaminoethanol, in the presence of a copper salt and trialkylsilyl halide.

In said process, step b) may be performed under any one or combination of the reaction conditions as defined herein, and for the preparation of any of the compounds of Formula 1a, 1b, Compound 1 or any one of the compounds as described in the examples. Where said process relates to the preparation of a compound of Formula 1a or 1b, and where $R^a$ is not ethyl, but selected from 1-hydroxyethyl, isopropyl, and n-propyl, it follows that cyclosporin A in step a) may be replaced with cyclosporin C, D or G as appropriate.

The compounds and intermediates of present disclosure may exist in various stereoisomeric forms and mixtures. In addition to stereocenters designated or depicted in the formulae, the disclosure may also include their enantiomers, diastereomers, racemates or other mixtures, as well as polymorphs, solvates, hydrates, complexes, free form, or salt forms. Unless otherwise indicated, the compounds within the scope of the current disclosure comprising one or more asymmetric centers which have not been designated or depicted in the formulae, or which have not been specifically named/described may also include all enantiomers, diastereomers, or their mixtures, racemic or otherwise thereof. Also included may be the use of any optically pure or stereochemically pure stereoisomers, as well as any combination of stereoisomers, as determined by methods well-known in the art. Optionally, the compounds of the invention may also include their isotopes, such compounds wherein an atom is replaced with an isotope, such as hydrogen with a deuterium, or a carbon with carbon-13.

As defined herein, a pharmaceutically acceptable compound is a compound which is generally safe, non-toxic and neither biologically nor otherwise undesirable, and is acceptable and compatible for pharmaceutical use in humans. A pharmaceutically acceptable salt is a salt of a compound, which retains its biological properties and which is non-toxic and is compatible for pharmaceutical use.

Compound 1, or a compound of Formula 1a or 1b may be obtainable by a process according any one or combination of the embodiments as described herein. The general process as described for preparation of Compound 1 may also be applied to the preparation of other, or related cyclosporin analogues. These may be prepared for example, by a process comprising first a step of reacting a cyclosporin compound (e.g. cyclosporin C, D, G, or other analogues) with dipyridyl disulphide to form a thiopyridyl intermediate (e.g. [(2'-(2-thiopyridyl)-Sar]³-cyclosporin C, or D, or G, etc), followed by a second step comprising the reaction of this intermediate with an amino alcohol compound in the presence of a copper salt, e.g. copper triflate and a trialkylsilyl halide such as TMSCl, in accordance with the embodiments described herein.

In a further aspect, the compounds prepared by a process (i.e. Compound 1, or compound of Formula 1a or 1b) as defined in any one or combination of embodiments as described herein above may be used for the prevention and/or treatment of diseases or medical conditions. They may be further used in the manufacture of a medicament for prevention and/or treating a disease or medical condition. Examples of diseases or conditions include, but are not limited to diseases or condition associated with cell, tissue or organ injury.

The following examples serve to illustrate the invention, however should not to be understood as restricting the scope of the invention.

EXAMPLES

Example 1—Preparation of Compound 1

Step 1: Compound 2, or [2'-(2-Thiopyridyl)-Sar]³-cyclosporin A) can be prepared from cyclosporin A according to the general method described in WO 2019/016572.

Step 1
LDA, LiCl

Cyclosporin A

-continued

Compound 2

Step 2

Cu Salt
Molecular Sieves

Compound 1

Step 2: The reaction of Compound 2 with dimethylami-noethanol to prepare Compound 1 was run under various conditions, as outlined in Table 1 and analyzed by HPLC.

A solution of compound 2 (97.8% purity) and dimethyl-aminoethanol in anhydrous THF was prepared and added to a suspension of copper triflate (vacuumed-dried), and if present, molecular sieves, or further reagent in anhydrous THF under an inert atmosphere. Before use, the copper triflate, molecular sieves were dried, e.g. under vacuum. The resulting reaction mixture was stirred at r.t. for 16 h, after which the reaction mixture was analyzed by HPLC.

2

1

B

A

TABLE 1

| No. | 2 | a | Cu(OTf)$_2$ | Reagent | Reaction Conditions | Result (HPLC) | | | |
|---|---|---|---|---|---|---|---|---|---|
| | | | | | | 1 | A | B | 2 |
| 1 | 1 g | 4.3 eq | 3.6 eq | 3Å molecular sieves | THF/10 ml; rt/16 h | 62.2% | 17.7% | 4.5% | 0.2% |
| 2 | 0.5 g | 4.3 eq | 3.6 eq | — | THF/5 ml; rt/16 h | 22.5% | 57.7% | 4% | 7.2% |
| 3 | 0.5 g | 4.3 eq | 3.6 eq | 0.9 eq acetyl chloride | THF/5 ml; rt/16 h | 4.6% | 19.7% | 0.3% | 67.7% |
| 4 | 1 g | 4.3 eq | 3.6 eq | 3Å molecular sieves; 0.9 eq TMSCl | THF/10 ml; rt/16 h | 71.6% | 4.9% | 4.5% | 0.2% |

Compound 1 can be prepared using the method according to the art in the presence of molecular sieves as a drying agent (Table 1, entry no. 1), however it was observed that that a significant amount of Compound 2 is converted to Sar-3-hydroxy cyclosporin A as a byproduct (A). The production of large amounts of undesired byproducts is undesirable from a cost-perspective and also due to additional purification burden.

The omission of molecular sieves from the reaction process, however, did not reduce conversion to the hydroxy adduct (see Table 1, entry no. 2). It was unexpectedly found, however, that the addition of a trialkylsilyl halide compound, i.e. trimethylsilyl chloride (TMSCl) as a reagent was able to improve efficiency of the conversion of Compound 2 to Compound 1 (see Table 1, entry no. 4). In contrast the use of acetyl chloride as a water scavenger reduced the rate of reaction, and furthermore had no impact with respect to reducing the formation of the hydroxy byproduct A (see Table 1, entry no. 3).

It was found that the addition of between 1.8 to 2.4 equivalents of trimethylsilyl chloride (TMSCl) to the reaction mixture improved the efficiency of the conversion of Compound 2 to Compound 1, even in the absence of molecular sieves as a drying agent. Less than ca. 10% of the hydroxy cyclosporin byproduct A was observed to be formed in the reaction process (see Table 2).

An improved reaction profile was observed in comparative reaction runs performed in the presence of TMSCl compared to molecular sieves (see Table 3); these reactions were conducted using the same batch of Compound 2 and reaction reagents. The reactions were performed under substantially anhydrous conditions. Before the reactions were performed, Compound 2 was dried at 60° C. under vacuum, Cu(OTf)$_2$ and the molecular sieves (4 Å) were dried under vacuum at 120° C. for 4 hours.

Reaction 1: A solution of Compound 2 and dimethylaminoethanol in THF was added to a flask containing Cu(OTf)$_2$ and THF at 0° C. TMSCl was added, and reaction mixture was allowed to warm to room temperature and stirred for 16 h.

Reaction 2: A solution of Compound 2 and dimethylaminoethanol in THF was added to a flask containing Cu(OTf)$_2$ and 4 Å molecular sieves in THF at 0° C. The reaction mixture was allowed to warm to room temperature and stirred for 16 h.

The reactions were performed in duplicate. The crude reaction mixtures were analyzed by HPLC (Thermo Hypersil GOLD™, Dim. 250×4.6 mm, Particle size 5 μm, column temperature 40° C., Phase A: 1000 mL H$_2$O+0.5 mL Formic Acid/Phase B: 1000 mL acetonitrile+0.5 mL formic acid).

TABLE 2

| Batch No. | Cpmd 2 (97.8% purity) | a | Cu(OTf)$_2$ | TMSCl | Reaction Conditions | Result (HPLC) | | | |
|---|---|---|---|---|---|---|---|---|---|
| | | | | | | 1 | A | B | 2 |
| 1 | 1 g | 0.29 g 4.3 eq | 0.99 g 3.6 eq | 0 eq | THF/10 ml; rt/16 h | 44.6% | 36.1% | 4.5% | 0% |
| 2 | 1 g | 0.29 g 4.3 eq | 0.99 g 3.6 eq | 124 mg 1.5 eq | THF/10 ml; rt/16 h | 63.7% | 11.5% | 5.2% | 0.3% |
| 3 | 1 g | 0.29 g 4.3 eq | 0.99 g 3.6 eq | 150 mg 1.8 eq | THF/10 ml; rt/16 h | 68.9% | 4.5% | 5.3% | 0.1% |
| 4 | 1 g | 0.29 g 4.3 eq | 0.99 g 3.6 eq | 174 mg 2.1 eq | THF/10 ml; rt/16 h | 64.5% | 7.2% | 5.7% | 0% |
| 5 | 1 g | 0.29 g 4.3 eq | 0.99 g 3.6 eq | 199 mg 2.4 eq | THF/10 ml; rt/16 h | 68.2% | 3.5% | 5.1% | 0% |

TABLE 3

| Run | | | | | Reaction | Result (HPLC) | | | |
|---|---|---|---|---|---|---|---|---|---|
| No. | 2 | a | Cu(OTf)$_2$ | Additive | Conditions | 1 | A | B | 2 |
| 1 | 1 g | 4.3 eq | 3.6 eq | TMSCl 2.4 eq | THF/10 mL; 0° C. to rt | 70.69% | 6.06% | 6.51% | 0% |
| 2 | 1 g | 4.3 eq | 3.6 eq | TMSCl 2.4 eq | THF/10 mL; 0° C. to rt | 68.17% | 5.72% | 7.24% | 0% |
| 3 | 1 g | 4.3 eq | 3.6 eq | 4Å MS 2.0 g | THF/10 mL; 0° C. to rt | 37.37% | 29.28% | 7.62% | 0% |
| 4 | 1 g | 4.3 eq | 3.6 eq | 4Å MS 2.0 g | THF/10 mL; 0° C. to rt | 36.81% | 29.59% | 7.37% | 0% |

It was observed that the formation of the hydroxy cyclosporin byproduct from Compound 2 was significantly reduced when TMSCl was used as an additive instead of molecular sieves.

Example 2—Preparation of Compound 1 (100-g Scale)

A solution of Compound 2 (100 g) and dimethylamino-ethanol (28.54 g, 4.3 eq) in THF was added to a reaction vessel comprising Cu(OTf)$_2$ (dried, 99.26 g, 3.6 eq) and trimethylsilyl chloride (19.88 g, 2.4 eq) in anhydrous THF (total volume 1000 mL). The resulting reaction mixture was stirred at room temperature for 16 h. After 16 hours, the reaction mixture quenched with water. The crude reaction mixture was analysed by HPLC (HPLC results: 66.3% Compound 1, 6.1% A and 3.5% B, and 0% Compound 2).

The aqueous phase was extracted with i-PrOAc. The organic phase was washed twice with aqueous solution of malic acid. The aqueous phase was combined and adjusted the pH value to 8 and extracted again with i-PrOAc. The combined organic phase was washed with brine, dried over magnesium sulfate, concentrated, and purified by column chromatography to provide 75.22 g of Compound 1 (76.5% yield); characterization was in line with literature references e.g. WO 2019/016572 A1; $^1$H-NMR (400 MHz CDCl$_3$, δ (ppm)): 6.01, sarcosine resonance.

Example 3—Preparation of Cyclosporin Analogues

The procedure described for the preparation of Compound 1 in Example 2 was applied as a general to prepare analogue compounds based on other amino alcohol intermediates (see Table 4). LC-MS analysis of the crude reaction mixtures demonstrated that in all reactions that the amount of the hydroxy-cyclosporin A byproduct which was formed remained low.

TABLE 4

| | Amino Alcohol | Product(s) | | Byproduct A |
|---|---|---|---|---|
| 1 | | | 54.34% | 1.38% |
| | | | 34.86% | |
| 2 | | | 74.05% | 7.16% |
| 3 | | | 48.38% | 13.82% |
| | | | 28.05% | |
| 4 | | | 22.07% | 4.01% |
| | | | 59.06% | |

Additional compounds are prepared based on the methodology of Example 2 as follows:

G25

Cu(OTf)₂, TMSCl, THF

2

-continued

3

The Cu(OTf)$_2$ catalyst (5.0 g, 16.39 mmol) is placed in 15 mL THF and cooled down to 0° C. A solution of Compound 2 (5.0 g, 3.81 mmol) and the amino alcohol compound G25 (1.9 g, 16.39 mmol) in 35 mL THF was added to the flask. TMSCl (1.0 g, 9.15 mmol) was finally added dropwise to the mixture. The mixture was then stirred at 20-25° C. After 16 hours, the reaction mixture was poured into 150 mL of water. Aqueous K$_2$CO$_3$ was added to adjust the pH to 10. i-PrOAc (50 ml) was added to the mixture and insoluble were filtered off. The filtrate was extracted with i-PrOAc(50 mL*2). The organic phase was washed twice with aqueous solution of malic acid. The aqueous phase was combined and adjusted the pH value to 8, and extracted again with i-PrOAc. The organic phase was washed with brine, dried over magnesium sulfate, and concentrated to give 1.4 g of compound 3. The product was further purified via chromatography. Compound 3 (($^1$H-NMR (400 MHz CDCl$_3$, δ (ppm)): 5.90, sarcosine residue); HRMS Electrospray (M+1) 1317.80; 1318.70; mass according to isotope distribution 1316.94 (100%), 1317.94 (73.5%)).

2

-continued

4

Compound 4 was prepared under analogous conditions by reaction of Compound 2 with the amino alcohol compound H25. Compound 4 (($^1$H-NMR (400 MHz CDCl$_3$, δ (ppm)):

5.82, sarcosine residue); HRMS Electrospray (M+1) 1315.70; 1316.60; mass according to isotope distribution: 1314.93 (100%), 1315.93 (73.5%)).

2

5

Compound 5: To a stirred solution of 2 (1 g) and R$^1$ (338.2 mg) in 20 mL THF was first added to the flask, Cu(OTf)$_2$ (1 g) at 0° C. under N$_2$, to be followed by TMSCl (198 mg). The mixture was then stirred at RT under N$_2$ for 16 hours. The resulting mixture was poured into 20 mL water, and then 20 mL of i-PrOAc was added. The aqueous phase was adjusted to pH 8.0 by the addition of aq. K$_2$CO$_3$. The aqueous phase was separated and was extracted by another portion of i-PrOAc. The combined organic phase was washed twice with aqueous malic acid solution (840 mg malic acid in 20 mL water). After separation of the phases, the aqueous phase was adjusted to pH 8.0 with the addition of aqueous K$_2$CO$_3$. The aqueous solution was then extracted twice with 20 mL i-PrOAc. The organic phase was dried and concentrated to give 340 mg of the desired compound 5. Compound 5: (($^1$H-NMR (400 MHz CDCl$_3$, δ (ppm)): 6.08, sarcosine residue); HRMS Electrospray (M+1) 1303.7; 1304.6; mass according to isotope distribution: 1302.93 (100%), 1303.93 (72.5%)).

Compound 6 was prepared analogously according to the general method described above for compound 5 from compound 2 and R2 and obtained after further purification by chromatography. Compound 6 (($^1$H-NMR (400 MHz CDCl$_3$, δ (ppm)): 6.31, sarcosine residue); HRMS Electrospray (M+1) 1303.4, 1304.6; mass according to isotope distribution: 1302.93 (100%); 1303.93 (72.5%)).

The invention claimed is:

1. A process for the preparation of a compound of Formula 1a or a pharmaceutically acceptable salt thereof,

2

6

Formula 1a wherein
$R^a$ is ethyl, 1-hydroxyethyl, isopropyl, or n-propyl;
$R^1$ and $R^2$ are independently selected from H, $C_1$ to $C_6$ alkyl, or wherein $R^1$ and $R^2$ are joined together to form a $C_3$ to $C_6$ cycloalkyl or heterocycloalkyl ring;
$R^3$ and $R^4$ are independently selected from H, $C_1$ to $C_6$ alkyl, substituted $C_1$ to $C_6$ alkyl, aryl, substituted aryl, benzyl, carbonyl, carboxyl, sulfonyl; or wherein $R^3$ and $R^4$ are joined together to form a $C_3$ to $C_6$ cycloalkyl or heterocycloalkyl ring;
$R^5$ and $R^6$ are independently selected from H, $C_1$ to $C_6$ alkyl, substituted $C_1$ to $C_6$ alkyl, or wherein $R^5$ and $R^6$ are joined together to form a $C_3$ to $C_6$ cycloalkyl or heterocycloalkyl ring;
wherein the process comprises a step of reacting a compound of Formula 2a with an amino alcohol in the presence of a copper salt and a trialkylsilyl halide;
wherein the compound of Formula 2a is:

Formula 2a wherein $R^a$ is selected from ethyl, 1-hydroxyethyl, isopropyl, and n-propyl; and
wherein $R^b$ is aryl, substituted aryl, heteroaryl or substituted heteroaryl; and
wherein the amino alcohol is of Formula 3:

Formula 3 wherein $R^1$, $R^2$, $R^3$, $R^4$, $R^5$ and $R^6$ are as defined for Formula 1a.

2. The process according to claim 1, wherein the process is for the preparation of a compound of Formula 1b or a pharmaceutically acceptable salt thereof, Formula 1b wherein the process comprises a step of reacting a compound of Formula 2b with an amino alcohol in the presence of a copper salt and a trialkylsilyl halide;

wherein the compound of Formula 2b is:

Formula 2b

3. The process according to claim 1 wherein $R^b$ is a heteroaryl or substituted heteroaryl substituent, optionally selected from pyridine, pyrimidine, pyrazine, thiazole, oxazole, benzothiazole, and benzimidazole.

4. The process according to claim 1 wherein the compound of Formula 2a is:

and wherein R$^a$ is selected from ethyl, 1-hydroxyethyl, isopropyl, and n-propyl.

5. The process according to claim 2, wherein the compound of Formula 2b is:

and wherein R$^a$ is selected from ethyl, 1-hydroxyethyl, isopropyl, and n-propyl.

6. The process according to claim 1, wherein R$^1$ and R$^2$ are both hydrogen.

7. The process according to claim 1, wherein R$^a$ is ethyl.

8. The process according to claim 1, wherein at least one of R$^3$ and R$^4$ is methyl, or wherein are R$^3$ and R$^4$ is both methyl.

9. The process according to claim 1, wherein at least one of R$^5$ and R$^6$ is hydrogen, or wherein both R$^5$ and R$^6$ are hydrogen.

10. The process according to claim 1, wherein the amino alcohol is dimethylaminoethanol.

11. The process according to claim 1 wherein the compound of Formula 2a is reacted with the amino alcohol in the presence of between 1.8 to 2.4 equivalents of trialkylsilyl halide.

12. The process of claim 1, wherein the trialkylsilyl halide is trimethylsilyl chloride.

13. The process of claim 1, wherein the compound of Formula 2a is reacted with 4.3 equivalents of the amino alcohol in the presence of 2.4 equivalents of trimethylsilyl chloride and 3.6 equivalents of copper triflate.

14. A process for the preparation of Compound 1 or a pharmaceutically acceptable salt thereof:

Compound 1 wherein the process comprises a step of reacting Compound 2

Compound 2 with dimethylaminoethanol, in the presence of a copper salt and a trialkylsilyl halide.

15. The process of claim 14, wherein Compound 2 is reacted with 3 to 5 equivalents of dimethylaminoethanol.

16. The process according to claim 14, wherein the trialkylsilyl halide is trimethylsilyl chloride.

17. The process according to claim 14, wherein Compound 2 is reacted with dimethylaminoethanol in the presence of 1.8 to 2.4 equivalents of the trialkylsilyl halide, optionally trimethylsilyl chloride.

18. The process according to claim 14, wherein Compound 2 is reacted with 4.3 equivalents of the dimethylaminoethanol in the presence of 2.4 equivalents of trimethylsilyl chloride and 3.6 equivalents of copper triflate.

19. The process according to claim 1, wherein the reaction is conducted in the absence of molecular sieves.

20. A process for the preparation of Compound 1 or a salt thereof, wherein the process comprises the steps of:

a) reacting cyclosporin A with a disulfide compound optionally pyridyl disulfide, in the presence of a base; and b) reacting a product of step a) with dimethylaminoethanol, in the presence of a copper salt, optionally copper triflate, and a trialkylsilyl halide, optionally trimethylsilyl chloride.

21. The process according to claim 2, wherein the compound of Formula 2b is reacted with the amino alcohol in the presence of between 1.8 to 2.4 equivalents of trialkylsilyl halide.

\* \* \* \* \*